United States Patent [19]

Findeisen et al.

[11] Patent Number: 4,594,441

[45] Date of Patent: Jun. 10, 1986

[54] PROCESS FOR THE PREPARATION OF URETHANES

[75] Inventors: Kurt Findeisen, Odenthal; Klaus König, Leverkusen; Rudolf Fauss, Cologne; Peter Heitkämper, Dormagen, all of Fed. Rep. of Germany

[73] Assignee: Bayer Aktiengesellschaft, Leverkusen, Fed. Rep. of Germany

[21] Appl. No.: 610,063

[22] Filed: May 14, 1984

Related U.S. Application Data

[63] Continuation of Ser. No. 198,316, Oct. 20, 1980, abandoned.

[30] Foreign Application Priority Data

Oct. 27, 1979 [DE] Fed. Rep. of Germany ....... 2943549

[51] Int. Cl.$^4$ ................... C07C 125/06; C07C 125/07
[52] U.S. Cl. ........................................ 560/25; 560/24; 560/27; 560/29; 560/30; 560/31; 560/32; 560/115; 560/157; 560/158; 560/160; 560/161
[58] Field of Search ....................... 560/24, 25, 27, 28, 560/29, 30–32, 115, 157, 158, 160–161

[56] References Cited

U.S. PATENT DOCUMENTS

| | | | |
|---|---|---|---|
| 2,409,712 | 10/1946 | Schweitzer | 260/453 |
| 2,806,051 | 9/1957 | Brockway | 260/471 |
| 3,098,093 | 7/1963 | Hagemeyer, Jr. et al. | 560/234 |
| 3,950,285 | 4/1976 | Wolgemuth | 260/18 |

OTHER PUBLICATIONS

Groggins, Unit Processes in Organic Synthesis, 5th Ed. 1958, McGraw-Hill-New York, p. 713.
"The Reactions of Carbamates with Alcohols", Journal of Organic Chemistry, pp. 1632–1637.
"Synthetic Organic Chemistry", Wagner et al., (1953), pp. 486–487 and 647.
Volodarskaya et al, Chem. Absts., 81, 64083(j), 1974.
Sal'nikova et al, Chem. Absts., 69, 85886(r), 1968.
Kraft, J.A.C.S., 70, 3570 (1948).

Primary Examiner—Howard T. Mars
Attorney, Agent, or Firm—Gene Harsh; Joseph C. Gil; Lyndanne M. Whalen

[57] ABSTRACT

A process for the preparation of urethanes. Urethanes having the general formula $R_1(NHCOOR_2)_n$ are reacted with an alcohol at a temperature of 120° to 400° C. in amounts such that, for every mol of the urethane, at least one mol of the alcohol is present. $R_1$ is a radical obtained by removing the isocyanate groups from an n-functional organic isocyanate, which isocyanate has a boiling point greater than 100° C. at atmospheric pressure. $R_2$ is a radical obtained by removing the hydroxyl group from a monohydric alcohol which has a boiling point greater than 140° C. at atmospheric pressure.

8 Claims, No Drawings

PROCESS FOR THE PREPARATION OF URETHANES

This application is a continuation, of application Ser. No. 198,316 filed Oct. 20, 1980 now abandoned.

BACKGROUND OF THE INVENTION

This invention relates to a process for the preparation of urethanes. More particularly, it relates to a process for making urethanes which are suitable starting materials for the preparation of isocyanates by thermal dissociation.

The preparation of urethanes without the use of phosgene and subsequent thermal dissociation thereof into the corresponding isocyanates is a valuable alternative to the preparation of isocyanates by phosgenation of the corresponding primary amines of the prior art. According to U.S. Pat. Nos. 2,409,712 and 2,806,051, this phosgene-free urethane synthesis takes place by reacting urea with primary amines and alcohols at a temperature greater than 100° C. It has been determined, however, that maximum yields are obtained when this synthesis is carried out at temperatures of 140° to 200° C. Therefore, when alcohols which boil at temperatures below the stated range are used in synthesizing urethanes, it is essential to carry out the process under pressure if maximum yields are desired. However, working under pressure requires an increased amount of apparatus and has the further disadvantage that the ammonia gas evolved during the reaction may not escape immediately after formation. The ammonia gas would dissolve in the reaction product and bring the reaction to a premature end, thereby causing poorer yields to be obtained. Consequently, attempts have been made to carry out the synthesis using comparatively high boiling alcohols so that it would be unnecessary to carry out the process under pressure. However, use of comparatively high boiling alcohols, e.g. alcohols, the boiling point of which is close to the boiling point of the isocyanate corresponding to the urethane, has the disadvantage that dissociation products (i.e., isocyanate and alcohols) are obtained from the subsequent thermal dissociation. These dissociation products are difficult to separate by distillation due to their similar boiling points. In the preparation of isocyanates by the thermal dissociation of urethanes, an immediate and effective separation of the dissociation products is critical in order to avoid recombination of the dissociation product.

SUMMARY OF THE INVENTION

It is an object of the present invention to provide a process for producing urethanes from alcohols which boil at temperatures above 140° C., which urethanes may be thermally dissociated into an isocyanate and alcohol which have boiling points sufficiently different to permit immediate separation thereof by distillation.

This object is achieved by reacting urethanes with an alcohol having a boiling point below 140° C. at an elevated temperature. The ability to carry out this type of "reurethanization" process is surprising because a heavier volatile component (higher boiling alcohol) has to be replaced by a lighter volatile component (lower boiling alcohol). It had been believed that urethanization was an irreversible reaction (see, J. Organic Chemistry 18 (1953), pages 1632–1633 and U.S. Pat. No. 3,950,285).

DESCRIPTION OF THE INVENTION

The present invention relates to a process for the preparation of urethanes which are suitable for use as starting materials in the preparation of organic isocyanates by means of thermal dissociation corresponding to the following general formula:

$R_1(NHCOOR_3)_n$ wherein
$R_1$ represents an organic radical obtained by removing the isocyanate groups from an n-functional organic isocyanate having a boiling point above 100° C. at atmospheric pressure,
$R_3$ represents a radical obtained by removing the hydroxyl group from a monohydric alcohol boiling at from 60° to 140° C. at atmospheric pressure, whereby the isocyanate corresponding to the general formula: $R_1(NCO)_n$, has a boiling point at least 30° C. higher at atmospheric pressure than the alcohol corresponding to the general formula: $R_3$—OH, and
n represents an integer of from 1 to 3.

Urethanes corresponding to the general formula:

$R_1(NHCOOR_2)_n$ are reacted with an alcohol having the general formula $R_3$—OH at 120°–400° C. in an amount such that, for every mol of the urethane $R_1(NHCOOR_2)_n$, at least one mol of the alcohol $R_3$—OH is present. $R_1$ and n are as defined above, and $R_2$ represents a radical obtained by removing the hydroxyl group from a monohydric alcohol having a boiling point above 140° C. at atmospheric pressure.

In preferred embodiments of this invention, the reaction is carried out in the presence of a catalyst and/or a solvent.

Starting materials for the process of the present invention include urethane compounds having from 1 to 3 N- and O-substituted urethane groups, the N-substituents of which correspond to the monofunctional or polyfunctional radical which has been obtained by removing the isocyanate groups from a monofunctional or polyfunctional isocyanate having a boiling point of above 100° C. at atmospheric pressure and the O-substituents of which correspond to the radical which has been obtained by removing the hydroxyl group from a monohydric alcohol boiling above 140° C. at atmospheric pressure, with the restriction that both of the above substituents are inert under the reaction conditions of the present process. Other starting materials are monohydric alcohols having boiling points of from 60° to 140° C. The boiling point of the monohydric alcohol at atmospheric pressure should be at least 10° C., preferably at least 50° C., below the boiling point of the alcohol upon which the urethane is based, and should also be at least 30° C. below the boiling point of the isocyanate upon which the urethane is based.

Each of the alcohols used, with the exception of the alcoholic hydroxyl group, should be inert under the conditions of the present process.

Suitable urethanes (a) are, for example, those corresponding to the following general formula:

$R_1(NHCOOR_2)_n$ wherein

R₁, R₂ and n are as defined above.

Urethanes which are preferred for the present process are those corresponding to the defined general formula, wherein

- $R_1$ represents an unsubstituted aliphatic hydrocarbon radical having from 6 to 18 carbon atoms, or a chloro-substituted aliphatic hydrocarbon radical having from 6 to 18 carbon atoms, or an aromatic hydrocarbon radical which is optionally methyl or chloro-substituted and/or which optionally has methylene bridges, having 6 to 15 carbon atoms, or a cycloaliphatic hydrocarbon radical having from 6 to 15, preferably from 6 to 10, carbon atoms, or an araliphatic hydrocarbon radical having from 7 to 15, preferably 7 or 8, carbon atoms,
- $R_2$ represents an optionally $C_1$-$C_4$ alkoxy or $C_1$-$C_4$ alkoxy-$C_2$-$C_4$ alkoxy-substituted or unsubstituted primary or secondary aliphatic hydrocarbon radical having from 5 to 18 carbon atoms, or a secondary cycloaliphatic hydrocarbon radical having from 6 to 15 carbon atoms, or preferably a cyclohexyl radical or a primary araliphatic hydrocarbon radical having from 7 to 15, preferably 7 or 8, carbon atoms, and
- n represents 1 or 2, and when n represents 2, at least 2 carbon atoms are positioned between the substituents NHCOOR₂ of the radical R₁.

Typical examples of urethanes suitable for the present process include: N-(n-hexyl)-O-(n-hexyl)-urethane; N-stearyl-O-cyclohexyl urethane; N-phenyl-O-cyclohexyl urethane; N-(p-tolyl)-O-benzyl urethane; N-(3,4-dichlorophenyl)-O-(2-phenylethyl)-urethane; 4,4'-bis-(hexoxycarbonylamino)-diphenylmethane; 2,4-bis-(cyclohexoxycarbonylamino)-toluene or 1-(cyclohexoxycarbonylamino)-3,5,5-trimethyl-5-(cyclohexoxycarbonylaminomethyl)-cyclohexane; e.g., the bis-urethane formally derived from 1 mol of isophorone diisocyanate and 2 mols of cyclohexanol.

Examples of alcohols (b) which are suitable for the present process are particularly those corresponding to the following general formula:

$$R_3—OH$$

wherein

R₃ is as defined above.

Preferred examples of such alcohols are those wherein R₃ represents a primary or secondary aliphatic hydrocarbon radical having from 1 to 4 carbon atoms. Typical examples of suitable alcohols corresponding to the defined general formula are methanol, ethanol, n-propanol, isopropanol, n-butanol and sec.-butanol.

In carrying out the process according to the present invention, the starting materials (a) and (b) are used in such amounts that, for each mol of the urethane (a), at least n mols, preferably from 5 n to 20 n mols, of the alcohol (b) are present, n being an integer from 1 to 3.

The process according to the present invention is carried out at a temperature of from 120° to 400° C. In the gas phase, the reaction takes place at a temperature of from 250° to 400° C., with 280° to 360° C. being the preferred range. When reacted in the liquid phase, the temperature is desirably 120° to 250° C., with a preferred range of 140° to 250° C., and the most preferred range of from 150° to 240° C. The reaction may be carried out in accordance with any one of the several methods.

The urethane reactant (a) may be dissolved in the low boiling alcohol (b) and continually reacted in the gas phase at a temperature of from 250° to 400° C. For example, the solution of the reactants may be continually introduced into a packed reaction tube, which tube is heated to the reaction temperature, whereupon the reaction takes place in the gas phase after the spontaneous evaporation of the starting solution. The gaseous mixture comprises the product urethane R₁(NHCOOR₂)ₙ, excess alcohol R₃—OH and separated alcohol R₂—OH. This gaseous mixture may then be accumulated at the outlet of the reaction tube and condensed in the liquid alcohol R₃—OH. The condensed mixture is then treated to isolate the product urethane in a manner which is described below.

The product urethane R₁(NHCOOR₃)ₙ may also be made by introducing the starting urethane (a) which is in a liquid or molten form into a reaction vessel which is maintained at from 120° to 250° C. A suitable reaction vessel will be equipped with a stirrer, a distillation bridge and an inlet tube. The alcohol (b) R₃—OH may then be added gradually, with constant stirring, with the temperature being maintained at from 120° to 250° C. The distillate produced is composed of excess nonreacted alcohol R₃—OH, separated alcohol R₂—OH and, depending on the vapor pressure of the product, the product urethane R₁(NHCOOR₃)ₙ. If a urethane is produced which is not volatile under the stated temperature conditions, then the product urethane will remain in the reaction vessel. The process is continued until no more alcohol R₂—OH is produced in the distillate. The product is then obtained in a pure form from the distillate or the residue. In a preferred embodiment of this method, the nonreacted excess alcohol R₃—OH should be separated from the resulting distillate and reused.

The urethane of the present invention may also be produced by heating a mixture of the starting urethane (a) and the low boiling alcohol (b) in an autoclave at from 120° to 250° C. When the reaction has finished, the content of the autoclave is treated in the manner described below to separate the product urethane R₁(NHCOOR₃)ₙ. The urethane having the general formula R₁(NHCOOR₃)ₙ may also be produced by continually pumping a solution of the starting urethane (a) in the low boiling alcohol (b) through a reactor (e.g., a tube or spiral reactor) at from 120° to 250° C., with the pressure in the reactor being adjusted so that the reaction mixture does not extensively evaporate.

The mixture leaving the reactor may then be treated in the manner described below to isolate the product urethane.

After carrying out the process of the present invention in accordance with methods such as those described above, the product is generally present in a mixture containing excess alcohol R₃—OH, separated alcohol R₂—OH and possibly small amounts of nonreacted starting urethane (a). The product is generally isolated from such a mixture by distillation, extraction or crystallization. In order to optimize the mixture produced by the present process, it is particularly advantageous and therefore preferred to use those alcohols R₃—OH which produce a urethane which has a boiling point that is at least 10° C., preferably at least 30° C., above or below (preferably above), the boiling point of the separated alcohol R₂—OH. Where such a difference in boiling points occurs, the reaction mixture of the present process is treated by a simple fractional distillation. In a typical fractional distillation separation, the excess alcohol R₃—OH will be the first fraction or distillation residue, the separated alcohol R₂—OH will be the second fraction or distillation residue and the product generally results as the third fraction or distillation residue. Where the product urethane is more volatile than the alcohol R₂—OH, however, the second fraction will be the product and the alcohol R₂—OH will be the third fraction or distillation residue. If the product urethane is not separated from a mixture by fractional distillation or if it is a nondistillable substance, then it may be purified, if required, by extraction or crystallization. Such an extraction or crystallization could be carried out with or without an auxiliary solvent. Suitable solvents are described below. As a result of the generally high yields of the present process, it is often unnecessary to separate the product from small amounts of starting urethane (a) which may still be present. Where the product urethane is made in a distillation reaction vessel as described above, such separation would be unnecessary.

It is normally unnecessary to use catalysts in carrying out the present process. However, it has been found that the use of catalysts in a quantity of from 1 ppm to 10% by weight, preferably from 100 ppm to 5% by weight, based on the starting urethane (a), often accelerates the reaction and may, therefore, be advantageous when carrying out the present process industrially.

Suitable catalysts include compounds known as esterification catalysts for organic carboxylic acids and the known catalysts for the isocyanate addition reaction. Suitable catalysts include Lewis acids and both inorganic and organic salts of transition metals such as zinc chloride, zinc acetate, zinc octoate, tin octoate, tin-II-chloride, tin-IV-chloride, dimethyl tin dilaurate, cobalt acetate, cobalt chloride, cobalt octoate, copper acetate, copper chloride, copper sulfate, lead acetate, lead chloride, iron-II-chloride or aluminum chloride.

The present process is normally carried out without the use of auxiliary solvents. However, it is possible to use auxiliary solvents such as toluene, xylene, chlorobenzene, dichlorobenzene, sulfolane, ε-caprolactam, petroleum ether, ethylene glycol dimethylether, ethylene glycol diethylether or nitrobenzene. Solvents of this type may also be used to purify the products by means of crystallization or recrystallization.

The products of the process claimed herein correspond to the following general formula:

$R_1(NHCOOR_3)_n$ where $R_1$, $R_3$ and n are as defined above.

Urethanes of high boiling alcohols may be converted into urethanes of low boiling alcohols in accordance with the present invention in a continuous or discontinuous manner. Circulation apparatus for the continuous production of these urethanes are known to those in the art.

These products are particularly suitable for use in the preparation of the isocyanates present therein in urethanized form by thermal dissociation.

Having thus described our invention, the following Examples are given by way of illustration. Unless indicated otherwise, the percentages given in these Examples relate to percent by weight.

EXAMPLES

EXAMPLE 1

657 g N-phenyl-O-cyclohexyl urethane (3 mols) were introduced into a reactor and heated to approximately 210° C. Methanol was continually pumped into the reactor from a stock vessel. Excess methanol, cyclohexanol and N-phenyl-methyl urethane where distilled off into a receiver vessel heated to 100° C. where the latter two components condensed. The methanol vapors were then condensed in a condenser and returned to the stock vessel.

The sump was distilled. In a continuous process, N-phenyl-O-cyclohexyl urethane could be continually fed to the reactor from another stock vessel at a rate commensurate with its conversion.

The reaction was complete after two hours. Cyclohexanol was distilled off in a water jet vacuum and 480 g of residue was obtained. 92.3 g % of this residue was N-phenyl-O-methyl urethane (HPLC). This residue was subjected to further distillation. 410 g N-phenyl-O-methyl urethane (90% of the theoretical yield) was obtained. The boiling point of the product urethane was 111°–113° C. at 0.26 mbar.

EXAMPLE 2

1105 g of N-phenyl-O-n-hexyl urethane (5 mols) were continuously converted with ethanol in N-phenylethyl urethane in accordance with the procedure described in Example 1. The temperature in the receiver vessel was 120° C. and the unreacted ethanol was continuously recycled. After completely emptying the stock vessel and the reactor, the reaction mixture was fractionally distilled. The yield of this process was 778 g N-phenyl-O-ethyl urethane (94% of the theoretical yield). The melting point of the product was 52° C. and its boiling point was 152° C. at 18 mbar.

EXAMPLE 3

1 mol of N-phenyl-O-cyclohexyl urethane was dissolved in 100 ml warm methanol and then reacted for thirty minutes at 320° C. in a pyrolysis tube 1 m long (with 40 mm clear width), filled with quartz rings. The reaction products were collected in 300 ml cold methanol with stirring. After extracting by distillation, 147 g of O-methyl-N-phenyl urethane were obtained having a purity of 98%.

EXAMPLE 4

748 g of 2,4-bis-(cyclohexoxycarbonylamino)-toluene (2 mols) were dissolved in 1.5 l isopropanol. The resultant solution was then pumped continually into a spiral reactor heated to 220° C. The pressure was adjusted to 10 bars and the product was continually collected. The residue time of the solution in the reactor may be varied within wide limits. The excess isopropanol and cyclohexanol was distilled off from the reaction mixture and the yield was determined by high pressure liquid chromatography (HPLC).

602 g of residue were obtained. 96% of this residue was 2,4-bis-(isopropoxycarbonylamino)-urethane.

EXAMPLE 5

368 g of 1,6-bis-(cyclohexoxycarbonylamino)-hexane (1 mol) were dissolved in 1.5 l ethanol and heated for two hours at 230° C. in a 3 l autoclave. After cooling, the reaction mixture was separated from the excess ethanol and resultant cyclohexanol in a water jet vacuum. The reaction product was examined by high pressure liquid chromatography (HPLC). A yield of 240 g of 1,6-bis-(ethoxycarbonylamino)-hexane was produced corresponding to a yield of 92% of the theoretical yield.

EXAMPLE 6

229 g of N-(n-hexyl)-O-cyclohexyl urethane were added to 1 l methanol in a 1.7 l autoclave and heated to 220° C. for 1.5 hours. After cooling, methanol and cyclohexanol were drawn off and the contents of the residue were determined and identified by IR, KR and HPLC. 149 g of N-(n-hexyl)-O-methyl urethane (94% of the theoretical yield) were produced.

EXAMPLE 7

16 mols O-cyclohexyl-N-phenyl urethane were dissolved in 16 l ethanol and heated for one hour at 230° C. in an autoclave. According to the high pressure liquid chromatogram, the O-cyclohexyl-N-phenyl urethane was reurethanized to an extent of 97% into O-ethyl-N-phenyl urethane. The mixture was then treated by distillation. 2.5 kg of O-ethyl-N-phenyl urethane were produced having 96.5% purity. In 220 g of the residue, there was 38% of O-ethyl-N-phenyl urethane, 6.2% N,N'-diphenyl urea and 52.4% O-cyclohexyl-N-phenyl urethane.

EXAMPLE 8

486 g (1 mol) of 4,4'-bis-[(2-butoxy-)ethoxycarbonylamino]-diphenylmethane and 1 l of ethanol are heated under pressure for one hour to 230° C. The reaction mixture was then allowed to cool to room temperature and excess ethanol was distilled off. The distillation residue was analysed by HPLC and found to consist of 0.95 mols of 4,4'-bis-(ethoxycarbonylamino-)diphenylmethane which corresponds to 95% of the theoretical yield.

What is claimed is:

1. A process for the preparation of urethanes which are suitable as starting materials for the preparation of organic isocyanates by means of thermal dissociation, said urethanes corresponding to the following general formula:

$$R_1(NHCOOR_3)_n$$

wherein
  $R_1$ represents a radical obtained by removing the isocyanate groups from an n-functional organic isocyanate having a boiling point above 100° C. at atmospheric pressure,
  $R_3$ represents a radical obtained by removing the hydroxyl group from a monohydric alcohol boiling at from 60° to 140° C. at atmospheric pressure with the isocyanate $R_1(NCO)_n$ having a boiling point which is at least 30° C. higher, at atmospheric pressure, than the alcohol $R_3$—OH, and
  n represents an integer of from 1 to 3, characterized in that
  (a) a urethane corresponding to the following general formula:

$$R_1(NHCOOR_2)_n$$

wherein
  $R_1$ and n are as defined above, and
  $R_2$ represents a radical obtained by removing the hydroxyl group from a monohydric alcohol having a boiling point above 140° C. at atmospheric pressure,
  is introduced in liquid or molten form into a reaction vessel maintained at from 120° to 250° C.,
  (b) gradually adding the alcohol $R_3$—OH while maintaining the temperature at from 120° to 250° C., and
  (c) removing a distillate made up of excess unreacted alcohol $R_3OH$, separated alcohol $R_2OH$ and depending on the vapor pressure of the product, product urethane $R_1(NHCOOR_3)_n$
  which process is continued until the alcohol $R_2OH$ is no longer produced and the product urethane $R_1(NHCOOR_3)_n$ may be recovered in pure form from the distillate or from the residue.

2. The process of claim 1, in which the amount of the alcohol $R_3$—OH is such that, for every mol of urethane $R_1(NHCOOR_2)_n$, from 5 n to 20 n mols of the alcohol are present.

3. The process of claim 2, characterized in that urethanes corresponding to the following gneral formula:

$$R_1(NHCOOR_2)_n$$

wherein
  $R_1$ represents an n-functional, optionally chloro-substituted, aliphatic hydrocarbon radical having from 6 to 18 carbon atoms, or an aromatic hydrocarbon radical having from 6 to 15 carbon atoms, which is optionally methyl or chloro-substituted and/or which optionally has methylene bridges, or a cycloaliphatic hydrocarbon radical having from 6 to 15 carbon atoms, or an araliphatic hydrocarbon radical having from 7 to 15 carbon atoms,
  $R_2$ represents an optionally $C_1$-$C_4$ alkoxy or $C_1$-$C_4$ alkoxy-$C_2$-$C_4$ alkoxy-substituted or unsubstituted primary or secondary aliphatic hydrocarbon radical having from 5 to 18 carbon atoms, or a secondary cycloaliphatic hydrocarbon radical having from 6 to 15 carbon atoms or a primary araliphatic hydrocarbon radical having from 7 to 15 carbon atoms, and
  n represents 1 or 2, and alcohols corresponding to the following general formula:

$$R_3-OH$$

wherein
  $R_3$ represents a primary or secondary aliphatic hydrocarbon radical having from 1 to 4 carbon atoms,
are used.

4. The process of claim 3, wherein a catalyst taken from the group consisting of Lewis acids and organic or inorganic salts of transition metals is used.

5. The process of claim 3, wherein the alcohol $R_3$—OH is reacted with the urethane $R_1(NHCOOR_2)_n$ in the presence of a solvent.

6. The process of claim 1, characterized in that urethanes corresponding to the following general formula:

$$R_1(NHCOOR_2)_n$$

wherein
  $R_1$ represents an n-functional, optionally chloro-substituted, aliphatic hydrocarbon radical having from 6 to 18 carbon atoms, or an aromatic hydrocarbon radical having from 6 to 15 carbon atoms, which is optionally methyl or chloro-substituted and/or which optionally has methylene bridges, or a cycloaliphatic hydrocarbon radical having from 6 to 15 carbon atoms, or an araliphatic hydrocarbon radical having from 7 to 15 carbon atoms, $R_2$ represents an optionally $C_1$–$C_4$ alkoxy or $C_1$–$C_4$ alkoxy-$C_2$–$C_4$ alkoxy-substituted or unsubstituted primary or secondary aliphatic hydrocarbon radical having from 5 to 18 carbon atoms, or a secondary cycloaliphatic hydrocarbon radical having from 6 to 15 carbon atoms or a primary araliphatic hydrocarbon radical having from 7 to 15 carbon atoms, and n represents 1 or 2, and alcohols corresponding to the following general formula:

$$R_3\text{---}OH$$

wherein $R_3$ represents a primary or secondary aliphatic hydrocarbon radical having from 1 to 4 carbon atoms, are used.

7. The process of claim 1, wherein a catalyst taken from the group consisting of Lewis acid and organic and inorganic salts of transition metals is used.

8. The process of claim 1, wherein the alcohol $R_3$—OH is reacted with the urethane $R_1(NHCOOR_2)_n$ in the presence of a solvent.

* * * * *